United States Patent [19]

Bell et al.

[11] 4,196,296

[45] Apr. 1, 1980

[54] CYCLOPENTA[C]PYRROLE DERIVATIVES

[75] Inventors: Malcolm R. Bell; Rudolf Oesterlin, both of East Greenbush, N.Y.

[73] Assignee: Sterling Drug Inc., New York, N.Y.

[21] Appl. No.: 862,944

[22] Filed: Dec. 21, 1977

Related U.S. Application Data

[60] Division of Ser. No. 772,003, Feb. 25, 1977, Pat. No. 4,126,620, which is a continuation-in-part of Ser. No. 703,949, Jul. 9, 1976, Pat. No. 4,098,797, which is a division of Ser. No. 558,807, Mar. 17, 1975, Pat. No. 4,008,250, which is a continuation-in-part of Ser. No. 346,005, Mar. 29, 1973, Pat. No. 3,928,380.

[51] Int. Cl.$^2$ .................................... C07D 401/04
[52] U.S. Cl. .................................... 546/272; 546/270
[58] Field of Search ...... 260/295 K, 295 SB, 294.8 C; 546/270, 272

[56] References Cited

PUBLICATIONS

Jain et al., "Chem. Abstracts", vol. 53 (1959), pp. 12275–12276.

*Primary Examiner*—Alan L. Rotman
*Assistant Examiner*—R. W. Ramsuer
*Attorney, Agent, or Firm*—William G. Webb; B. Woodrow Wyatt

[57] ABSTRACT

2,4,5,6-Tetrahydrocyclopenta[c]pyrrole-4-carboxamide and 4-thiocarboxamide derivatives useful as anti-secretory and anti-ulcer agents are prepared by hydrolysis or thiohydrolysis of the corresponding 2,4,5,6-tetrahydrocyclopenta[c]pyrrole-4-carbonitriles or, in the case of the thiocarboxamides, by reaction of the 4-carboxamide with phosphorus pentasulfide.

5 Claims, No Drawings

CYCLOPENTA[C]PYRROLE DERIVATIVES

RELATED APPLICATIONS

This is a division of our prior, copending application Ser. No. 772,003, filed Feb. 25, 1977 now U.S. Pat. No. 4,126,620, patented Nov. 21, 1978 which in turn is a continuation-in-part of our prior, copending application Ser. No. 703,949, filed July 9, 1976, now U.S. Pat. No. 4,098,797, patented July 4, 1978, which in turn is a division of our prior application Ser. No. 558,807, filed Mar. 18, 1975, now U.S. Pat. No. 4,008,250, patented Feb. 15, 1977, which in turn is a continuation-in-part of our prior application Ser. No. 346,005, filed Mar. 29, 1973, now U.S. Pat. No. 3,928,380, patented Dec. 23, 1975.

BACKGROUND OF THE INVENTION (a) Field of the Invention

This invention relates to 2,4,5,6-tetrahydrocyclopenta[c]pyrrole-4-carboxamides and thiocarboxamides useful as anti-secretory and anti-ulcer agents.

(b) Description of the Prior Art

Although the 2,4,5,6-tetrahydrocyclopenta[c]pyrrole ring system is known (see for example Volz et al., Tetrahedron Letters 47, 4111–14 (1969) who disclose 1,3-dimethyl- and 1,2,3-trimethyl-4-oxo-2,4,5,6-tetrahydrocyclopenta[c]pyrrole and Berger et al., J. Org. Chem. 35, 3122 (1970) who disclose 1,3-dimethyl-4-oxo-2,4,5,6-tetrahydrocyclopenta[c]pyrrole), derivatives of such ring system having exocyclic functions, other than methyl groups at the 1-, 2- and 3-positions, have not been previously known. Furthermore the aforementioned prior art species are prepared by laborious multistep synthetic methods and are not known to have any utility except as laboratory curiosities.

SUMMARY OF THE INVENTION

In a composition of matter aspect, the invention relates to certain 1,3-di-$R_6$-2-$R_7$-4-$R_3$-6-$R_4$-6-$R_5$-2,4,5,6-tetrahydrocyclopenta[c]pyrrole-4-carboxamides and thiocarboxamides where $R_3$, $R_4$, $R_5$, $R_6$ and $R_7$ are hydrogen, lower-alkyl or other organic groups more specifically defined hereinafter, which are useful as anti-secretory and anti-ulcer agents.

DETAILED DESCRIPTION INCLUSIVE OF THE PREFERRED EMBODIMENTS

More specifically, the invention relates to 2,4,5,6-tetrahydrocyclopenta[c]pyrrole-4-carboxamides and 4-thiocarboxamides, which are useful as anti-secretory and anti-ulcer agents and which have the Formula I:

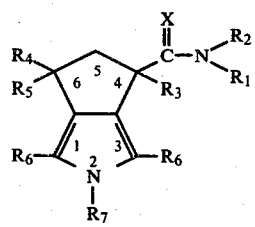

where X is O or S; $R_1$ is hydrogen, lower-alkyl, di-lower-alkylamino-lower-alkyl, morpholino-lower-alkyl, 1-pyrrolidyl-lower-alkyl or 1-piperidyl-lower-alkyl; $R_2$ is hydrogen or lower-alkyl, or the group

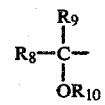

can represent a 1-imidazolyl group; each of $R_3$, $R_4$ and $R_5$ is hydrogen or methyl; each $R_6$ group is the same or different hydrogen, formyl (CHO) and lower-alkane-1,3-diol ketals thereof, phenyl-lower-alkyl, carboxy, carbo-lower-alkoxy, carbo-lower-alkoxy-lower-alkyl, carbo-lower-alkoxy-lower-alkenyl, carboxy-lower-alkyl, carboxy-lower-alkenyl, methyl, lower-alkenyl or a group of the formula:

$$R_8-\underset{\underset{OR_{10}}{|}}{\overset{\overset{R_9}{|}}{C}}-$$

where $R_8$ is hydrogen, lower-alkyl, lower-alkenyl, lower-alkynyl, phenyl or phenyl-lower-alkyl; $R_9$ is hydrogen, cyano (CN), lower-alkyl, lower-alkenyl, lower-alkynyl, phenyl, phenyl-lower-alkyl, carboxy, carbo-lower-alkoxy, carbamyl ($CONH_2$), aminomethyl ($CH_2NH_2$), lower-alkanoyl, trichloromethyl, carbo-lower-alkoxy-lower-alkyl or carbo-lower-alkoxy-lower-alkynyl; $R_{10}$ is hydrogen, benzoyl, lower-alkanoyl, carboxy-lower-alkanoyl (and ammonium salts thereof) or lower-alkyl, $R_{10}$ being other than hydrogen only when either one or both of $R_8$ and $R_9$ are hydrogen and $R_9$ being cyano only when $R_{10}$ is hydrogen; and $R_7$ is hydrogen, lower-alkyl, halo-lower-alkyl, lower-alkenyl, lower-alkynyl, di-lower-alkyl-amino-lower-alkyl, morpholino-lower-alkyl, 1-pyrrolidyl-lower-alkyl, 1-piperidyl-lower-alkyl, carbo-lower-alkoxy-lower-alkyl, carboxy-lower-alkyl, carboxamido-lower-alkyl, thiocarboxamido-lower-alkyl, lower-alkoxy-lower-alkyl, hydroxy-lower-alkyl, lower-alkyl-thio-lower-alkyl, cycloalkyl, cycloalkyl-lower-alkyl, 2-, 3- or 4-pyridyl, phenyl, phenyl-lower-alkyl, thienyl, 9-acridinyl, 4-(2,1,3-benzothiadiazolyl), 2-benzothiazolyl, 3-carbazolyl, 2-benzoxazolyl, 2- or 6-purinyl, 2-pyrazinyl, 4-pyrimidinyl, 2-thiazolyl, 3-pyrazolyl, 2- or 6-pyrimidinyl, 2-benzimidazolyl, 2-benzothiazolyl, 5-, 6- or 7-indazolyl, 5-isoquinolinyl, 3-pyridazinyl, 2-thiadiazolyl, 5-tetrazolyl, 2-thiazolinyl, 3-(1,2,4-triazinyl), 3-(1,2,4-triazolyl), or divalent-lower-alkylene having its valences on different carbon atoms and joining two of the 2,4,5,6-tetrahydrocyclopenta[c]pyrrole moieties together, and wherein the phenyl, benzoyl and phenyl-lower-alkyl groups can be further substituted in the phenyl nucleus by a single methylenedioxy or lower-alkyl group or by from one to three, the same or different, members of the group consisting of lower-alkyl, halogen (including fluorine, bromine and chlorine), hydroxy, trifluoromethyl, lower-alkanoylamino, amino, di-lower-alkylamino, di-lower-alkyl-aminomethyl, carboxy, carboxamido, carbo-lower-alkoxy, lower-alkyl-mercapto, lower-alkylsulfinyl, lower-alkylsulfonyl, nitro and sulfamoyl, except that both $R_6$ groups are not simultaneously hydrogen and further except that when $R_7$ is unsubstituted phenyl and $R_6$ at the 3-position and $R_8$ are both hydrogen, $R_9$ is not unsubstituted-phenyl. The two species defined by the latter excepting clauses have been found to be inactive in one or both of the anti-secretory and anti-ulcer tests as has also a species where $R_7$ is di-lower-alkoxy-substituted-phenyl.

Preferred compounds within the ambit of Formula I are those where X is O, each of $R_1$ and $R_2$ is hydrogen or lower-alkyl; each of $R_3$, $R_4$ and $R_5$ is methyl; both $R_6$ groups are lower-alkyl; and $R_7$ is lower-alkyl or phenyl and also the compounds of formula I where X is O; $R_1$ and $R_2$ are each hydrogen; $R_3$, $R_4$ and $R_5$ are each methyl; one $R_6$ is hydrogen, lower-alkyl or hydroxymethyl and the other is hydrogen, lower-alkyl or the group:

where $R_8$ is hydrogen, lower-alkyl, lower-alkenyl, or lower-alkynyl; and $R_7$ is phenyl (or substituted-phenyl), both of which preferred groups are represented by the formula:

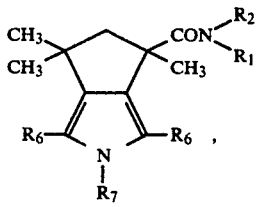

except that both $R_6$ groups are not simultaneously hydrogen.

As used herein the terms "lower-alkyl" and "lower-alkoxy" mean saturated, monovalent, aliphatic radicals, including straight or branched-chain radicals, of from one to four carbon atoms as illustrated by, but not limited to, methyl, ethyl, propyl, isopropyl, butyl, sec.-butyl, isobutyl, methoxy, ethoxy, propoxy, isopropoxy, butoxy, isobutoxy, and the like.

As used herein the term "cycloalkyl" means saturated carbocyclic groups containing from three to six ring carbon atoms and having a total of five to ten carbon atoms, as illustrated by, but not limited to, cyclopropyl, cyclobutyl, 2-methylcyclobutyl and cyclohexyl.

As used herein the terms "lower-alkenyl" and "lower-alkynyl" mean monovalent, aliphatic radicals of from three to six carbon atoms which contain at least one double or triple bond, and are either straight or branched-chain as illustrated by, but not limited to, 1-(2-propenyl), 1-(1-propenyl), 1-(3-methyl-2-propenyl), 1-(1,3-dimethyl-2-propenyl), 1-(2-hexenyl), 1-(2-propynyl) and 1-(2-butynyl).

As used herein, the term "lower-alkylene" means divalent, aliphatic radicals, including straight or branched-chain radicals, of from one to eight carbon atoms, and having its valences on different carbon atoms as illustrated by, but not limited to, methylene, 1,2-ethylene, 1,4-butylene, 1,6-hexylene, 3-methyl-1,5-pentylene and 1,8-octylene.

As used herein, the terms "lower-alkenylene" and "lower-alkynylene" mean divalent, aliphatic radicals of from two to six carbon atoms which contain at least one double or triple bond and can be straight or branched, as illustrated by, but not limited to, 1,2-ethenyl, 1,2-ethynyl, 1,4-(2-butenyl), 1,4-(2-butynyl), 1,6-(2-hexenyl) and 1,6-(2-hexynyl).

The compounds of Formula I where X is O; $R_1$ and $R_2$ are each hydrogen; and $R_3$, $R_4$, $R_5$, $R_6$ and $R_7$ have the meanings given above are prepared by hydrolysis, under acid, basic or neutral conditions, of the corresponding 2,4,5,6-tetrahydrocyclopenta[c]pyrrole-4-carbonitriles having the Formula II:

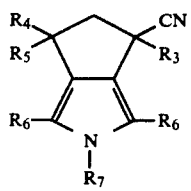

where $R_3$, $R_4$, $R_5$ and $R_6$ have the meanings given above, and $R_7$, in addition to the various meanings given above, represents cyano-lower-alkyl. Hydrolysis under basic conditions is advantageously effected by warming a solution of the nitrile of Formula II in an inert organic solvent, for example methanol, ethanol or isopropanol, containing a molar excess of an alkali metal hydroxide. Hydrolysis in a neutral medium is advantageously carried out using the procedure of Bennett et al., J. Am. Chem. Soc. 95, 3030–1 (1973) in which a planar, nonionic tertiary phosphine metal-hydroxy complex is used as a catalyst. Hydrolysis in an acid medium is carried out by heating a solution of the nitrile in a mineral acid, for example, phosphoric acid, polyphosphoric acid or aqueous sulfuric acid at a temperature from 0° C. to around 70° C. During the reaction, the nitrile group in the compounds of Formula II where $R_7$ is cyano-lower-alkyl is hydrolyzed simultaneously with the nitrile group attached to the 4-position of the 2,4,5,6-tetrahydrocyclopenta[c]pyrrole to thus produce compounds of Formula I where $R_7$ is carboxamido-lower-alkyl, and the above-described procedure constitutes a preferred method of preparing the latter compounds.

The compounds of Formula I where X is S; $R_1$ and $R_2$ are each hydrogen; and $R_3$, $R_4$, $R_5$, $R_6$ and $R_7$ have the meanings given above are preferably prepared by thiohydrolysis of the nitriles of Formula II using the procedure of Karrer et al., Helv. Chim. Acta 28, 820 (1945) which involves reacting the nitrile with a saturated solution of ammonia and hydrogen sulfide in an organic solvent, preferably a lower-alkanol, at room temperature. Alternatively, the reaction can be carried out under pressure in an autoclave at a temperature from 150°–160° C. using the procedure described by Ralston et al. J. Org. Chem. 4, 68 (1939). As in the case of the hydrolysis of the compounds of Formula II to those of Formula I where X is O, thiohydrolysis of the compounds of Formula II where $R_7$ is cyano-lower-alkyl affords the compounds of Formula I where $R_7$ is thiocarboxamido-lower-alkyl, and the above-described procedure constitutes a preferred method of preparing the latter compounds.

Alternatively, and preferably, the compounds of Formula I where X is S are prepared by reaction of the corresponding compounds where X is O with phosphorus pentasulfide. The reaction is carried out by heating the reactants directly either with or without a solvent. Preferred solvents, when used, are benzene, toluene, xylene, dioxane and the like.

The compounds of Formula I where $R_7$ is other than hydrogen can also be prepared by reaction of the corresponding compounds where $R_7$ is hydrogen with a strong base, for example alkali metal hydrides or alkali metal amides, in an inert organic solvent, for example dimethylsulfoxide, dioxane, dimethylformamide, tetrahydrofuran, dibutyl ether, and the like, and reaction of the resulting salt with an appropriate alkylating agent, $R_7X$, where X is the anion of a strong mineral acid, for example a hydrogen halide or sulfuric acid, and $R_7X$, where X is the anion of a strong mineral acid, for example a hydrogen halide or sulfuric acid, and $R_7$ has the meanings given above. The reaction is preferably carried out at low temperatures, i.e. from 0° C. to about 40° C. During the reaction, alkylation can take place at either the amide nitrogen atom, when compounds where $R_1$ and $R_2$ are both hydrogen are used as starting materials, or at the pyrrole nitrogen atom, and it is possible to isolate both isomeric products from the reaction mixture.

The compounds of Formula I where $R_7$ is lower-alkenyl are preferably prepared by Hofmann elimination of a tertiary amine from a compound of Formula I where $R_7$ is di-lower-alkylamino-lower-alkyl, morpholino-lower-alkyl, 1-pyrrolidyl-lower-alkyl or 1-piperidyl-lower-alkyl. The method comprises converting the tertiary amine to a quaternary ammonium salt by reaction of the amine with an ester of a strong inorganic acid, e.g. a lower-alkyl halide or a di-lower-alkyl sulfate, and reacting the quaternary salt with silver oxide, preferably in an aqueous medium to effect conversion of the quaternary salt to the corresponding ammonium hydroxide, which spontaneously decomposes in an aqueous medium at ambient temperature to the N-lower-alkenyl-substituted compound of Formula I and a tertiary amine. It is preferred to use a dimethylamino-lower-alkyl substituted compound of Formula I as starting material and a methyl halide or dimethyl sulfate as quaternizing agent.

The compounds of Formula I where $R_1$ and/or $R_2$ are other than hydrogen and $R_7$ is other than hydrogen are prepared by reacting the corresponding carboxamides where either one or both of $R_1$ and $R_2$ are hydrogen with a strong base, for example an alkali metal hydride or an alkali metal amide, followed by reaction of the resulting salt with an alkylating agent, for example a lower-alkyl halide or a di-lower-alkyl sulfate. As indicated above, when compounds where both $R_1$ and $R_2$ are hydrogen are used as starting materials, alkylation can take place on both the ring and amide nitrogen atoms, necessitating separation of the isomeric products. Preparation of the compounds where both $R_1$ and $R_2$ are lower-alkyl is best effected by stepwise alkylation of the carboxamide, that is alkylation of the compounds where both $R_1$ and $R_2$ are hydrogen using one mole of a strong base and one mole of an alkylating agent followed by a second alkylation of the resulting N-lower-alkylcarboxamide where one of $R_1$ and $R_2$ is lower-alkyl. The reaction with a second mole of strong base takes place under much more vigorous conditions involving use of higher reaction temperatures, i.e. from about 50° C. to about 150° C., and longer reaction times than the above-described method for alkylation at the pyrrole nitrogen atom or monoalkylation at the amide nitrogen atom, which take place at lower temperatures and shorter reaction times. The reaction is carried out in an inert organic solvent, for example dimethylsulfoxide, dioxane, dimethylformamide, tetra-hydrofuran, dibutyl ether, and the like.

The compounds of Formula I where one or both $R_6$ groups are hydroxymethyl ($R_8$, $R_9$, and $R_{10}$ are hydrogen), are prepared by reduction, with an alkali metal borohydride, of the corresponding compounds of Formula I where one or both $R_6$ groups are formyl. The reaction is carried out in an inert organic solvent, for example lower-alkanols, dioxane, diethyl ether, and the like. The reaction generally takes place at ambient temperature, although elevated temperatures up to the boiling point of the solvent can be used to expedite the reaction. The method for the preparation of compounds where both $R_6$ groups are hydroxymethyl is represented by the equation:

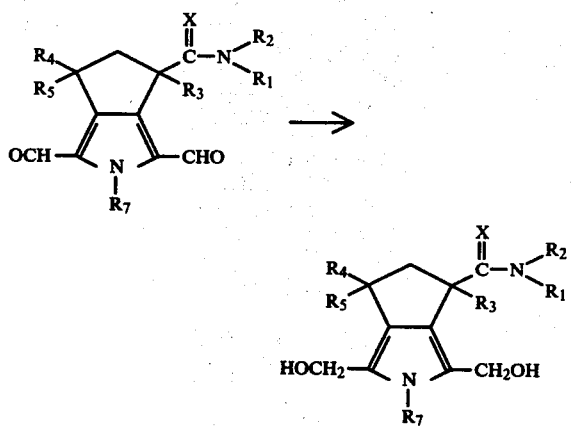

where $R_1$, $R_2$, $R_3$, $R_4$, $R_5$, $R_7$, and X have the meanings given above.

The compounds of Formula I where one or both $R_6$ moieties is the group

where $R_8$ is hydrogen and $R_9$ is lower-alkyl, lower-alkynyl, lower-alkenyl, phenyl, phenyl-lower-alkyl, trichloromethyl, carbo-lower-alkoxy-lower-alkylene or carbo-lower-alkoxy-lower-alkynylene are prepared by reaction of the corresponding compound where one or both $R_6$ groups is formyl with an organo metallic compound such as an organo lithium, e.g. a lower-alkyl, lower-alkenyl, lower-alkynyl or phenyl lithium, or an organo magnesium halide, e.g. phenyl (or substituted-phenyl) magnesium halide or a phenyl-lower-alkyl magnesium halide, and hydrolysis of the resulting organometallic compound. The reaction is carried out in an inert organic solvent such as tetrahydrofuran or diethyl ether.

The compounds of Formula I where one or both $R_6$ groups is lower-alkenyl are prepared by heating the corresponding carbinol where $R_8$ is hydrogen and $R_9$ is lower-alkyl in an organic solvent, for example benzene, toluene or xylene. In some cases recrystallization of the carbinols from such boiling solvents is sufficient to effect dehydration.

The compounds of Formula I where $R_8$ is lower-alkyl, lower-alkynyl, lower-alkenyl, phenyl or phenyl-lower-alkyl and $R_9$ is the same or different lower-alkyl, lower-alkynyl, lower-alkenyl, phenyl or phenyl-lower-alkyl are prepared by reacting the corresponding compounds where $R_6$ is carbo-lower-alkoxy with either four molar equivalents of an organo metallic compound as indicated above, which affords compounds where $R_8$ and $R_9$ are identical, or if desired only two moles of the organo metallic compound can be used which affords compounds where $R_6$ is a ketone group, i.e. $R_8$—CO (or $R_9$—CO). The latter is then reacted with two moles of a different organo metallic compound to give the carbinols where $R_8$ and $R_9$ are different. In each of the above-described reactions requiring use of an organo metallic compound, one mole of the organo metallic reagent in addition to that required for reaction at the 1- or 3-positions is required when the compounds of Formula I where one or both of $R_1$ and $R_2$ is hydrogen is used as the starting material, because one mole of the organo metallic reagent reacts with one of the protons on the amide nitrogen.

The compounds of Formula I where $R_9$ is cyano, carbamyl or aminomethyl are prepared via the cyanohydrin (i.e. $R_9$ is cyano) of the corresponding compounds where $R_6$ is formyl. The cyanohydrins are prepared by reaction of the formyl compounds with diethyl aluminum cyanide in an inert organic solvent, for example benzene, toluene, xylene, tetrahydrofuran, dioxane or mixtures of these solvents. A preferred solvent is a mixture of benzene and tetrahydrofuran. The cyanohydrins in turn, on either hydrolysis with dilute sulfuric acid using the same conditions as described for hydrolysis of the compounds of Formula II to Formula I, or catalytic reduction with hydrogen over platinum oxide afford, respectively, the compounds where $R_9$ is carbamyl and aminomethyl.

The compounds of Formula I where $R_9$ is carboxy or carbo-lower-alkoxy are prepared by hydrolysis of the corresponding compounds where $R_9$ is trichloromethyl, using the procedure described below for preparing the compounds where $R_6$ is formyl or carboxy, to afford the compounds where $R_9$ is carboxy. The esters are prepared from the acids by standard esterification procedures.

The compounds of Formula I where $R_9$ is lower-alkanoyl are prepared by hydroxylation of the corresponding compounds where $R_9$ is lower-alkynyl using dilute sulfuric acid.

The compounds of Formula I where $R_{10}$ is lower-alkyl are prepared by reacting the free carbinols ($R_{10}$ is hydrogen) with a lower-alkanol in the presence of a mineral acid. The compounds where $R_{10}$ is an ester group, i.e. benzoyl, lower-alkanoyl or carboxy-lower-alkanoyl are prepared by reacting the carbinol either with an acid halide or an acid anhydride in the presence of an acid acceptor, for example pyridine or a tri-lower-alkylamine.

The compounds of Formula I where one or both $R_6$ groups are carboxy are prepared by oxidizing the corresponding compounds where one or both $R_6$ groups are formyl with one mole of an oxidizing agent per formyl group, for example alkaline permanganate. When it is desired to prepare compounds of Formula I where one $R_6$ group is formyl and the other is carboxy, then compounds where both $R_6$ groups are formyl are used, and one of the two formyl groups must be individually protected while other transformations are carried out on the other formyl group after which the protecting group is removed to regenerate the formyl group which can then either be preserved in the final products or if desired utilized as a handle for conversion to other groups such as various carbinols as described above. A particularly effective means of protecting one or two formyl groups is to convert the latter to a ketal by reaction of the formyl derivative with one molar equivalent of an alkanediol (or with two molar equivalents of a lower-alkanol) in an anhydrous medium and in the presence of a strong acid. Preferred alkanediols are 1,3-propanediols which may be straight or branched, for example, 2,2-dimethyl-propanediol or 1,1,3-trimethyl-1,3-propanediol (i.e. 2-methylpentane-2,4-diol). The resulting mixture of products containing a ketal group at each of the 1- and 3-positions can, if desired, be separated into the individual components, and each component treated separately in subsequent synthetic steps. The unprotected formyl group can then, for example, be oxidized to the carboxylic acid using an alkaline medium in which the ketal group is stable, for example alkaline permanganate. The carboxyl group thus produced can either be retained as such or converted to an ester moiety or, if desired, it can be removed by heating the product at a temperature of around 200°–250° C. in a high boiling organic solvent, for example dimethylaniline, ethylene glycol or propylene glycol.

The corresponding compounds of Formula I where one $R_6$ group is formyl and the other a carboxy group can also be prepared by reaction of the corresponding compound of Formula I where both $R_6$ groups are methyl with five molar equivalents of sulfuryl chloride, which affords the compounds where one $R_6$ group is dichloromethyl and the other trichloromethyl, and hydrolysis of the latter with water in a water-miscible organic solvent as described above. The compounds where one or both $R_6$ groups are carbo-lower-alkoxy are prepared from compounds wherein one or both $R_6$ groups are carboxy by standard esterification procedures comprising reacting the carboxylic acid with a lower-alkanol.

The compounds of Formula I where $R_1$ and $R_2$ are each hydrogen can also be prepared by reduction with one molar equivalent of diisobutyl aluminum hydride (DIBAL) of the compounds of Formula II, and oxidation with oxygen of the resulting cyclopenta[c]pyrrole-4-aldimide having the Formula III without isolation of the latter. The method is illustrated by the following reaction sequence:

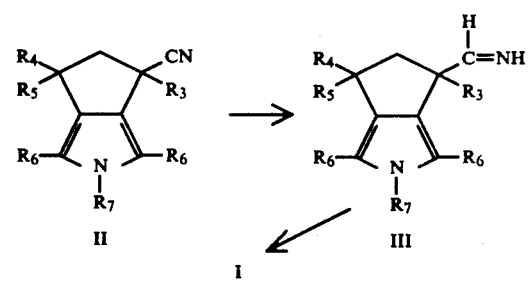

where $R_3$, $R_4$, $R_5$, $R_6$ and $R_7$ have the meanings given above.

The compounds of Formula III can also be converted to the final products of Formula I where $R_1$ and $R_2$ are hydrogen and X is O by reacting the aldimide of Formula III with a peracid, e.g. performic, peracetic or perbenzoic acid, to produce an oxaziridine having the Formula IV, which on thermal or photochemical decomposition by irradiation with light affords the compounds of Formula I. The method is represented by the reaction sequence:

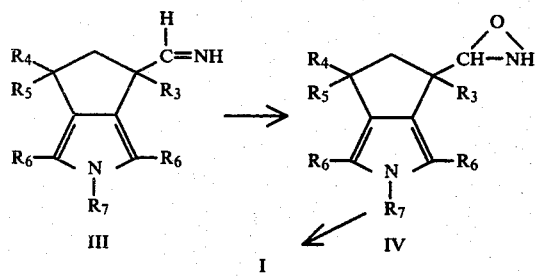

where $R_3$, $R_4$, $R_5$, $R_6$ and $R_7$ have the meanings given above.

Still another method for converting the carbonitriles of Formula II to the carboxamides of Formula I where $R_1$ and $R_2$ are hydrogen and X is O comprises oxidizing the carbonitrile with peroxide, e.g. hydrogen peroxide, in a basic medium, e.g. in the presence of an alkali metal hydroxide, and decomposition of the resulting perimidate of Formula V by heating the reaction medium. A preferred solvent is acetone. The method is represented by the reaction sequence:

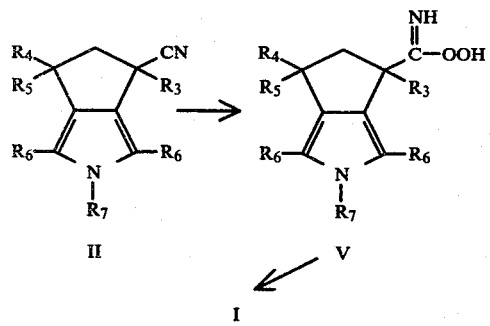

where $R_3$, $R_4$, $R_5$, $R_6$ and $R_7$ have the meanings given above.

The intermediate 2,4,5,6-tetrahydrocyclopenta[c-]pyrrole-4-carbonitriles of Formula II are prepared by a variety of different methods depending upon the identities of the various $R_3$, $R_4$, $R_5$, $R_6$ and $R_7$ groups. These methods are described in detail in U.S. Pat. No. 4,008,250, patented Feb. 15, 1977 on application Ser. No. 558,807 identified above as a "RELATED APPLICATION", the disclosure of which is incorporated herein by reference.

The novel compounds of the instant invention are the compounds of Formula I and includes the acid-addition salts of the compounds which contain a basic, salt-forming group such as di-lower-alkylamino-lower-alkyl, morpholino-lower-alkyl, 1-pyrrolidyl-lower-alkyl, 1-piperidyl-lower-alkyl, aminomethyl, di-lower-alkylaminomethyl or a basic heterocyclic group such as pyridyl. The compounds of Formula I in free base form are converted to the acid-addition salt form by interaction of the base with an acid in an organic solvent and isolating the salt directly or by concentration of the solution. In like manner, the free base can be regenerated from the acid-addition salt form in the conventional manner, that is by treating the salts with cold, weak aqueous bases, for example alkali metal carbonates and alkali metal bicarbonates. The bases thus regenerated can then be interacted with the same or a different acid to give back the same or a different acid-addition salt. Thus the original bases and all of their acid-addition salts are readily interconvertible.

In standard biological test procedures, described generally by Shay et al., Gastroenterology 5, 43 (1945) and 26, 906 (1954), the compounds of Formula I have been found to possess anti-secretory and anti-ulcer activity and are thus useful as anti-secretory and anti-ulcer agents. The anti-secretory and anti-ulcer test procedures used are fully described in our U.S. Pat. No. 4,008,250.

The compounds of Formula I were thus found to inhibit secretion of gastric fluids and to inhibit reserpine-induced stomach ulceration when administered in a dose range of from around 10 mg./kg. to around 200 mg./kg. The compounds are preferably administered orally, and the amount of a particular compound to be administered, either alone or as the essential active ingredient in a formulation, will range from about 10 to about 200 mg./kg.

The actual determination of the numerical biological data definitive for a particular compound of Formula I is readily determined by standard test procedures by technicians versed in pharmacological test procedures without the need for any extensive experimentation.

The compounds of Formula I can be prepared for use by incorporation in unit dosage form as tablets or capsules for oral administration either alone or in combination with suitable adjuvants such as calcium carbonate, starch, lactose, sodium bicarbonate, sodium lauryl sulfate, sugar, dextrose, mannitol, cellulose, gum acacia, and the like. Alternatively, they can be formulated for oral administration in aqueous alcohol, glycol, or oil solutions or oil-water emulsions in the same manner as conventional medicinal substances are prepared. They can also be formulated for oral use with foodstuffs or admixed with foodstuffs for veterinary use.

The molecular structures of the compounds of the invention were assigned on the basis of study of their infrared, ultraviolet, and NMR spectra, and confirmed by the correspondence between calculated and found values for elementary analyses for the elements.

The following examples will further illustrate the invention without, however, limiting it thereto. All melting points are uncorrected.

EXAMPLE 1

A mixture of 22 g. (0.10 mole) of 2,4,5,6-tetrahydro-1,2,3,4,6,6-hexamethylcyclopenta[c]pyrrole-4-carbonitrile in 10 ml. of water and 100 ml. of concentrated sulfuric acid was warmed to 85° C. on a steam bath and heated with stirring for about five minutes. The resulting dark brown solution was poured into water, basified with 35% aqueous sodium hydroxide until no further solid separated, and the solid which precipitated was collected, washed with water, air dried, and recrystallized with charcoaling from ethyl acetate to give 17.3 g. of 2,4,5,6-tetrahydro-1,2,3,4,6,6-hexamethylcyclopenta[c]pyrrole-4-carboxamide, m.p. 184.5°–187.5° C.

Following a procedure similar to that described in Example 1, using an appropriate 2,4,5,6-tetrahydro-4,6,6-trimethylcyclopenta[c]pyrrole-4-carbonitrile of Formula II, the following 2,4,5,6-tetrahydro-4,6,6-trimethylcyclopenta-[c]pyrrole-4-carboxamides of Formula I were prepared, where in each instance, $R_1$ and $R_2$ are each hydrogen; X is O; $R_3$, $R_4$ and $R_5$ are each $CH_3$; and where, unless noted otherwise by the notations "(1)" and "(3)" to indicate $R_6$ substituents in the 1- and 3-positions, respectively, both $R_6$ groups have the meanings indicated in the column headed "$R_6$".

Table 1a

| Example | $R_6$ | $R_7$ | Wt. II | Wt. I | m.p. (°C)/Solvent |
|---|---|---|---|---|---|
| 1A | $CH_3$ | H | 60 | 28 | 230–233/ethyl acetate |
| 1B | $CH_3$ | $CH_2CH_2CH_2N(CH_3)_2$ | 29.3 | 19 | 114.5–116/acetonitrile |
| 1C | $CH_3$ | —$(CH_2)_6$— | 45 | 10.5 | 218–221/DMF |
| 1D | $CH_3$ | $CH_2CH_2C_6H_5$ | 56 | 17.8 | 115.5–117.5/cyclohexane |
| 1E | $CH_3$ | 4-$NH_2SO_2C_6H_4$ | 44 | 1.8 | 258–260/methanol |
| 1F | $CH_3$ | $C_6H_5$ | 28 | 18 | 132–135/cyclohexane |
| 1G | $CH_3$ | $C_2H_5$ | 37.2 | 15.2 | 162–164/ethyl acetate |
| 1H | $CH_3$ | $C_3H_7$ | 40 | 34.4 | 164.5–166.5/isopropanol |
| 1J | $CH_3$ | $CH_2C_6H_5$ | 24 | 20.2 | 170–171/ethyl acetate |
| 1K | $CH_3$ | 4-$CH_3OC_6H_4$ | 70 | 37 | 198.5–201/isopropanol |
| 1L | $CH_3$ | 4-$CH_3C_6H_4$ | 58.4 | 32 | 198–202/acetonitrile |
| 1M | $CH_3$ | 4-$ClC_6H_4$ | 62.5 | 34 | 16.5–167.5/acetonitrile |
| 1N | $CH_3$ | 3-$ClC_6H_4$ | 81.4 | 60 | 139–142/acetonitrile |
| 1P | $CH_3$ | 2-pyridyl | 86 | 32 | 187–189/acetonitrile |
| 1Q | $CH_3$ | 3-$CH_3C_6H_4$ | 60 | 27.4 | 149.5–151.5/methanol |
| 1R | $CH_3$ | 2-$ClC_6H_4$ | 116 | 14.7 | 181–183/methanol |
| 1S | $CH_3$ | 2-$CH_3C_6H_4$ | 100 | 28 | 159–161/methanol |
| 1T | $CH_3$ | 4-$FC_6H_4$ | 88 | 54 | 150–151/isopropanol |
| 1U | $CH_3$ | 4-$(CH_3)_2NC_6H_4$ | 64.2 | 31.5 | 238–241/DMF |
| 1V | $CH_3$ | 4-$HOC_6H_4$ | 88.2 | 31.7 | 249–251/methanol |
| 1W | $CH_3$ | 4-$CH_3CONHC_6H_4$ | 55 | 22 | 236–239/methanol |
| 1X | $CH_3$ | $CH_2CH_2CONH_2$ | 23.9 | 4.3 | 130.5–133/acetone |
| 1Y | $CH_3$ | $C_4H_9$ | 30.7 | 7.8 | 135–137/cyclohexane |
| 1Z | $CH_3$ | iso-$C_3H_7$ | 25.6 | 13.5 | 156–158/cyclohexane |
| 1AA | $CH_3$ | $CH_2CH_2OC_2H_5$ | 103.1 | 21.5 | 109–111/hexane |
| 1AB | CHO | $C_6H_5$ | 10 | 3.4 | 164.5–166.5/methanol |
| 1AC | $CH_3$ | $CH_2COOC_2H_5$ | 55 | 33.5 | 138–140/ether-ethanol |
| 1AD | $CH_3$ | cyclohexyl | 81 | 31 | 125–150/isopropanol |
| 1AE | $CH_3$ | cyclopropyl | 12.1 | 10.1 | 188–192 |
| 1AF | $CH_3$ | cyclopentyl | 6.9 | 4.6 | 152–155/cyclohexane |
| 1AG | $CH_3$ | $CH_2CH_2N(CH_3)_2$ | 1.9 | 0.5 | 110–113/heptane-hexane |
| 1AH | $CH_3$ | $CH_2CH_2N(CH_2CH_2)_2O$ | 9.8 | 8.6 | 142–144/hexane |
| 1AJ | $CH_3$ | $CH_2CH_2CH_2OH$ | 2.6 | | |
| 1AK | $CH_3$ | cyclobutyl | 9.3 | 5.5 | 149–152 |
| 1AL | $CH_3$ | cyclopropyl-$CH_2$ | 25 | 10.9 | 150–153/ethanol-$H_2O$ |
| 1AM | $CH_3$ | sec-$C_4H_9$ | 40 | 29.3 | 152–154/cyclohexane |
| 1AN | $CH_3$ | iso-$C_4H_9$ | 18.5 | 12.0 | 148.5–151/hexane |
| 1AP | $CH_3$ | 3,4-$(HO)_2C_6H_3$ | 5.0$^{(a)}$ | 2.3 | 129–131/ethyl acetate-pentane |
| 1AQ | $CH_3$ | 4-$C_2H_5OC_6H_4$ | 45 | 8 | 212–214/ethanol-$H_2O$ |
| 1AR | $CH_3$ | 3-$CF_3C_6H_4$ | 6.3 | 4.0 | 150–153/benzene-pentane |
| 1AS | $CH_3$ | $CH_2C\equiv CH$ | 22.6 | 14.7 | 141–145/cyclohexane |
| 1AT | $CH_3$ | $CH_2CH_2F$ | 17.7 | 11.1 | 130–131/benzene-hexane |
| 1AU | $CH_3$ | $CH_2CH_2Cl$ | 20.0 | 17.3 | 145.5–147/benzene-hexane |
| 1AV | CHO(1) H(3) | $C_6H_5$ | 6.3 | 4.2 | 190–192/isopropanol |
| 1AW | CHO(1) $CH_3$(3) | $C_6H_5$ | 29.8 | 1.0 | 123–126/benzene |
| 1AX | CHO(1) COOH(3) | 4-$FC_6H_4$ | 6.1 | 1.0 | 241 (dec.)/methanol |
| 1AY | CHO(1) COOH(3) | $C_6H_5$ | 14.0 | 7.9 | 231–232/acetone |
| 1AZ | CHO(1) H(3) | 4-$FC_6H_4$ | 5.0 | 3.7 | 193–196/isopropanol |
| 1BA | $CH_3$(1) COOCH(3) | $C_6H_5$ | 3.0 | 3.1 | 121.5–123.5/ether-hexane |
| 1BB | $COOCH_3$(1) H(3) | $C_6H_5$ | 6.0 | 5.09 | 195–196.5/ether-hexane |
| 1BC | $CH_3$(1) $CH_2CH_2COOC_2H_5$(3) | $C_6H_5$ | 3.0 | 2.7 | 110–112/heptane |
| 1BD | $CH_3$(1) $CH=CHCOOC_2H_5$(3) | $C_6H_5$ | 4.0 | 1.3 | 172–174/hexane |
| 1BE | $CH=CHCOOC_2H_5$(1) H(3) | $C_6H_5$ | 4.5 | 1.3 | 197–198$^{(b)}$ |
| 1BF | $CH=CHCOOH$(1) H(3) | $C_6H_5$ | 4.5 | 1.4 | 210–212$^{(b)}$ |
| 1BG | $CH_3$ | 2-pyrazinyl | 1.0 | 1.1 | 169–171/acetonitrile |
| 1BH | $CH_3$ | 4-pyridyl | 3.5 | 3.1 | 118.5–120/acetonitrile |

Table 1a-continued

| Example | R$_6$ | R$_7$ | Wt. II | Wt. I | m.p. (°C.)/Solvent |
|---|---|---|---|---|---|
| 1BJ | CHO(1) H(3) | H | 15.0 | 4.0 | 117–119/heptane |
| 1BK | CH$_3$ | 4-C$_6$H$_4$COOC$_2$H$_5$ | 35 | 12.8 | 188–191/benzene-hexane |
| 1BL | CH$_3$ | 3-HOC$_6$H$_4$ | 10 | 1.5 | 216–218/ethyl acetate |
| 1BM | CH$_3$ | 3-(CH$_3$)$_2$N-4-HOC$_6$H$_3$ | 2.0 | 1.9 | 110–112/benzene$^{(c)}$ |
| 1BN | CH$_3$ | 3-HOC$_6$H$_3$-4-COOC$_2$H$_5$ | 11.0 | 8.4 | 170–172/benzene-hexane |
| 1BP | CH$_3$ | 4-HOC$_6$H$_3$-3-COOC$_2$H$_5$ | 9.0 | 3.3 | 172–174/ethanol |

$^{(a)}$Starting material was 1-[3,4-(2,2-propylenedioxy)phenyl] compound.
$^{(b)}$The products of Examples 1BE and 1BF were obtained as a mixture from the same starting material and were separated by partitioning between ethyl ether and ammonium hydroxide and each product isolated without recrystallization.
$^{(c)}$Contains one mole of benzene as solvate.

It is contemplated that by following a procedure similar to that described in Example 1, using an appropriate 2,4,5,6-tetrahydro-cyclopenta[c]pyrrole-4-carbonitrile of Formula II in refluxing 90% aqueous sulfuric acid, the following compounds of Formula I can be prepared where, in each instance, R$_1$ and R$_2$ are hydrogen; and X is 0.

Table 1b

| Example | R$_3$ | R$_4$ | R$_5$ | R$_6$ | R$_7$ |
|---|---|---|---|---|---|
| 1BQ | CH$_3$ | CH$_3$ | CH$_3$ | CH$_3$ | 4-BrC$_6$H$_4$ |
| 1BR | CH$_3$ | CH$_3$ | CH$_3$ | CH$_3$ | 2,4,6-Cl$_3$C$_6$H$_2$ |
| 1BS | CH$_3$ | CH$_3$ | CH$_3$ | CH$_3$ | 2-Cl-4-CH$_3$C$_6$H$_3$ |
| 1BT | CH$_3$ | CH$_3$ | CH$_3$ | CH$_3$ | 3,4-OCH$_2$OC$_6$H$_3$ |
| 1BU | CH$_3$ | CH$_3$ | CH$_3$ | CH$_3$ | 4-CF$_3$C$_6$H$_4$ |
| 1BV | CH$_3$ | CH$_3$ | CH$_3$ | CH$_3$ | 2,4,6-(CH$_3$)$_3$C$_6$H$_2$ |
| 1BW | CH$_3$ | CH$_3$ | CH$_3$ | CH$_3$ | CH$_2$CH$_2$SC$_2$H$_5$ |
| 1BX | CH$_3$ | CH$_3$ | CH$_3$ | C$_3$H$_7$ | C$_6$H$_5$ |
| 1BY | CH$_3$ | CH$_3$ | CH$_3$ | iso-C$_3$H$_7$ | C$_6$H$_5$ |
| 1BZ | CH$_3$ | CH$_3$ | CH$_3$ | C$_4$H$_9$ | C$_6$H$_5$ |
| 1CA | CH$_3$ | H | H | CH$_3$ | C$_6$H$_5$ |
| 1CB | CH$_3$ | H | H | CH$_3$ | CH$_3$ |
| 1CC | CH$_3$ | CH$_3$ | CH$_3$ | CH$_3$ | 4-NH$_2$C$_6$H$_4$ |
| 1CD | CH$_3$ | CH$_3$ | CH$_3$ | CH$_3$ | cyclohexyl-CH$_2$ |
| 1CE | CH$_3$ | CH$_3$ | CH$_3$ | CH$_3$ | CH$_2$CH$_2$N(CH$_2$)$_4$ |
| 1CF | CH$_3$ | CH$_3$ | CH$_3$ | CH$_3$ | CH$_2$CH$_2$N(CH$_2$)$_5$ |
| 1CG | H | H | H | CH$_3$ | CH$_3$ |
| 1CH | CH$_3$ | CH$_3$ | CH$_3$ | CH$_3$ | 2-thienyl |
| 1CJ | CH$_3$ | CH$_3$ | CH$_3$ | CH$_3$ | 3-H$_2$NCOC$_6$H$_4$ |
| 1CK | CH$_3$ | CH$_3$ | CH$_3$ | CH$_3$ | 3-CH$_3$SC$_6$H$_4$ |
| 1CL | CH$_3$ | CH$_3$ | CH$_3$ | CH$_3$ | 4-O$_2$NC$_6$H$_4$ |
| 1CM | CH$_3$ | CH$_3$ | CH$_3$ | C$_6$H$_5$CH$_2$ | C$_6$H$_5$ |
| 1CN | CH$_3$ | CH$_3$ | CH$_3$ | CH$_3$ | 3-pyridyl |
| 1CP | CH$_3$ | CH$_3$ | CH$_3$ | CH$_3$ | 9-acridinyl |
| 1CQ | CH$_3$ | CH$_3$ | CH$_3$ | CH$_3$ | 4-(2,1,3-benzo-thiazolyl) |
| 1CR | CH$_3$ | CH$_3$ | CH$_3$ | CH$_3$ | 2-benzothiazolyl |
| 1CS | CH$_3$ | CH$_3$ | CH$_3$ | CH$_3$ | 3-carbazolyl |
| 1CT | CH$_3$ | CH$_3$ | CH$_3$ | CH$_3$ | 2-benzoxazolyl |
| 1CU | CH$_3$ | CH$_3$ | CH$_3$ | CH$_3$ | 2-purinyl |
| 1CV | CH$_3$ | CH$_3$ | CH$_3$ | CH$_3$ | 6-purinyl |
| 1CW | CH$_3$ | CH$_3$ | CH$_3$ | CH$_3$ | 4-pyrimidinyl |
| 1CX | CH$_3$ | CH$_3$ | CH$_3$ | CH$_3$ | 2-thiazolyl |
| 1CY | CH$_3$ | CH$_3$ | CH$_3$ | CH$_3$ | 3-pyrazolyl |
| 1CZ | CH$_3$ | CH$_3$ | CH$_3$ | CH$_3$ | 2-pyrimidinyl |
| 1DA | CH$_3$ | CH$_3$ | CH$_3$ | CH$_3$ | 6-pyrimidinyl |
| 1DB | CH$_3$ | CH$_3$ | CH$_3$ | CH$_3$ | 2-benzimidazolyl |
| 1DC | CH$_3$ | CH$_3$ | CH$_3$ | CH$_3$ | 2-benzothiazolyl |
| 1DD | CH$_3$ | CH$_3$ | CH$_3$ | CH$_3$ | 5-indazolyl |
| 1DE | CH$_3$ | CH$_3$ | CH$_3$ | CH$_3$ | 6-indazolyl |
| 1DF | CH$_3$ | CH$_3$ | CH$_3$ | CH$_3$ | 7-indazolyl |
| 1DG | CH$_3$ | CH$_3$ | CH$_3$ | CH$_3$ | 5-isoquinolinyl |
| 1DH | CH$_3$ | CH$_3$ | CH$_3$ | CH$_3$ | 3-pyridazinyl |
| 1DJ | CH$_3$ | CH$_3$ | CH$_3$ | CH$_3$ | 2-thiadiazolyl |
| 1DK | CH$_3$ | CH$_3$ | CH$_3$ | CH$_3$ | 5-tetrazolyl |
| 1DL | CH$_3$ | CH$_3$ | CH$_3$ | CH$_3$ | 2-thiazolinyl |
| 1DM | CH$_3$ | CH$_3$ | CH$_3$ | CH$_3$ | 3-(1,2,4-triazinyl) |
| 1DN | CH$_3$ | CH$_3$ | CH$_3$ | CH$_3$ | 3-(1,2,4-triazolyl) |

EXAMPLE 2

A mixture of 25 g. (0.09 mole) of 2-phenyl-2,4,5,6-tetrahydro-1,3,4,6,6-pentamethylcyclopenta[c]pyrrole-4-carbonitrile, 100 ml. of absolute ethanol and 25 ml. of 35% aqueous sodium hydroxide was refluxed on a steam bath for seventy hours, and the mixture then diluted with 250 ml. of water. The oil which separated crystallized on cooling and was collected, washed, and dried to give 17 g. of 2-phenyl-2,4,5,6-tetrahydro-1,3,4,6,6-pentamethylcyclopenta[c]pyrrole-4-carboxamide, m.p. 123°–130° C. identical with the compound described above in Example 1F.

EXAMPLE 3

To a stirred mixture of 10.5 g. (0.24 mole) of a 57% dispersion of sodium hydride in mineral oil (which was washed and decanted with hexane to remove the mineral oil) in 100 ml. of dimethylsulfoxide was added a solution of 29.6 g. (0.1 mole) of 2-phenyl-2,4,5,6-tetrahydro-1,3,4,6,6-pentamethylcyclopenta[c]pyrrole-4-carboxamide dissolved in 200 ml. of dimethylsulfoxide. The reaction mixture was stirred for about one and a half hours until evolution of hydrogen ceased, and then treated dropwise with 35.5 g. (0.25 mole) of methyl iodide. After stirring for an additional two hours, the mixture was diluted with about 10 ml. of water, poured onto ice, and the white precipitate was removed by filtration. The filtrate was extracted with ether, added to an ether solution of the solid, and the combined organic solution washed several times with water, dried over sodium sulfate, and evaporated to dryness.

The resulting yellow oil (35.3 g.) was dissolved once again in 200 ml. of dimethylsulfoxide, added to a suspension of 6.0 g. of sodium hydride in dimethylsulfoxide, the mixture warmed to 75° C. for about five minutes, treated with 18 g. of methyl iodide as above, and then stirred for one hour at room temperature. The reaction mixture, when worked up in the manner described above, afforded 31.3 g. of a yellow oil which slowly crystallized and which was recrystallized from a methanol/water mixture to give 27.7 g. of 2-phenyl-2,4,5,6-tetrahydro-1,3,4,6,6-pentamethylcyclopenta[c]pyrrole-4-N,N-dimethylcarboxamide, m.p. 100°–104° C.

It is contemplated that by following a procedure similar to that described in Example 3, using an appropriate 2-R$_7$-2,4,5,6-tetrahydro-1,3,4,6,6-pentamethylcyclopenta[c]pyrrole-4-carboxamide and an appropriate lower-alkyl halide, the following compounds of Formula I can be prepared where, in each instance, R$_3$, R$_4$, R$_5$ and both R$_6$ groups are each CH$_3$, and X is 0.

Table 3

| Example | R$_1$ | R$_2$ | R$_7$ |
|---|---|---|---|
| 3A | CH$_3$ | H | CH$_3$ |
| 3B | CH$_3$ | CH$_3$ | CH$_3$ |
| 3C | CH$_3$ | H | CH$_2$CH$_2$CH$_2$N(CH$_3$)$_2$ |
| 3D | CH$_3$ | CH$_3$ | CH$_2$CH$_2$CH$_2$N(CH$_3$)$_2$ |

Table 3-continued

| Example | $R_1$ | $R_2$ | $R_7$ |
| --- | --- | --- | --- |
| 3E | $CH_3$ | H | $CH_2CH_2C_6H_5$ |
| 3F | $CH_3$ | $CH_3$ | $CH_2CH_2C_6H_5$ |
| 3G | $CH_3$ | H | $C_6H_5$ |
| 3H | $CH_3$ | H | 2-pyridyl |
| 3J | $CH_3$ | $CH_3$ | 2-pyridyl |

EXAMPLE 4

A 2.53 g. (0.06 mole) portion of a 57% dispersion of sodium hydride in mineral oil was washed free of mineral oil by slurrying and decantation with hexane, and was then slurried in 40 ml. of dimethylsulfoxide. To the mixture was added a solution of 8.8 g. (0.04 mole) of 2,4,5,6-tetrahydro-1,3,4,6,6-pentamethylcyclopenta[c]pyrrole-4-carboxamide (described above in Example 1A), and the mixture was stirred at room temperature for one hour. The mixture was then treated with 8.1 g. (0.06 mole) of cyclopropylmethyl bromide, stirred at room temperature overnight, poured into water, and the mixture extracted with diethyl ether. The ether extracts, on drying and evaporation to dryness, afforded a brown oil which was chromatographed on silica gel using a 3% isopropanol in ether solution as eluent. There was thus obtained a crystalline material which was slurried with ether/pentane to give 0.55 g. of 2-cyclopropylmethyl-2,4,5,6-tetrahydro-1,3,4,6,6-pentamethylcyclopenta[c]pyrrole-4-carboxamide, m.p. 145°–148° C. identical with that described above in Example 1AL.

EXAMPLE 5

To a solution of 4.45 g. (0.013 mole) of 2-phenyl-1-hydroxymethyl-3-carboxy-2,4,5,6-tetrahydro-4,6,6-trimethylcyclopenta[c]pyrrole-4-carboxamide in 15 ml. of dimethylformamide was added 0.61 g. (0.014 mole) of a 57% mineral oil dispersion of sodium hydride, the mixture was stirred for two hours and then treated with 0.8 g. of methyl iodide and stirred at ambient temperature for about twelve hours. The mixture was then poured into water, and the solid was collected and recrystallized from acetone to give 2.3 g. of 2-phenyl-1-hydroxymethyl-3-carbomethoxy-2,4,5,6-tetrahydro-4,6,6-trimethylcyclopenta[c]pyrrole-4-carboxamide, m.p. 226°–227° C.

EXAMPLE 6

A solution of 3.05 g. (0.01 mole) of 2-[3-(dimethylamino)propyl]-2,4,5,6-tetrahydro-1,3,4,6,6-pentamethylcyclopenta[c]pyrrole-4-carboxamide (described above in Example 1B) in 30 ml. of isopropanol was treated with 2.1 g. of methyl iodide, and the mixture was allowed to stand at room temperature overnight. The material which had separated was then collected, washed with isopropanol and pentane and dried to give 4.5 g. of 2-[3-(dimethylamino)propyl]-2,4,5,6-tetrahydro-1,3,4,6,6-pentamethylcyclopenta[c]pyrrole-4-carboxamide methiodide, m.p. 128°–130° C. A solution of 10.2 g. (0.06 mole) of silver nitrate in 102 ml. of hot water was treated with a solution of 2.34 g. of sodium hydroxide in 24 ml. of hot water. The resulting precipitate was washed five times by decantation with hot water, then filtered, and the solid added to a solution of about 9 g. (0.02 mole) of 2-[3-(dimethylamino)propyl]-2,4,5,6-tetrahydro-1,3,4,6,6-pentamethylcyclopenta[c]pyrrole-4-carboxamide methiodide in 60 ml. of water. The mixture was stirred at room temperature overnight, then filtered, the filter washed first with hot water and then with ethanol, the aqueous and the ethanol filtrates being set aside separately for further work. The ethanol washings were refiltered, evaporated to dryness, and the solid residue which slowly crystallized was set aside and combined with organic material obtained by evaporation to dryness of the aqueous filtrate, heating the solid residue on a steam bath for three hours under a vacuum pump, extraction of the residue with ethyl acetate and evaporation to dryness of the extracts. The combined material obtained from the aqueous and ethanol washings were recrystallized from ethyl acetate/pentane to give two crops totaling 0.7 g. of 2-allyl-2,4,5,6-tetrahydro-1,3,4,6,6-pentamethylcyclopenta[c]pyrrole-4-carboxamide, m.p. 96°–98° C.

EXAMPLE 7

To a suspension of 1.025 g. of 2-phenyl-2,4,5,6-tetrahydro-1,3-diformyl-4,6,6,-trimethylcyclopenta[c]pyrrole-4-carboxamide (described above in Example 1AB) in 10 ml. of ethanol was added with stirring a suspension of 250 mg. of sodium borohydride in ethanol, and the resulting clear solution was allowed to stand at room temperature for two hours. The white crystalline solid which separated was collected, washed with water and dried to give 645 mg. of product. This material was combined with that obtained by evaporation to dryness of the filtrate from the main product and trituration with water and collection and drying of the residual solid. There was thus obtained an additional 344 mg. of 2-phenyl-2,4,5,6-tetrahydro-1,3-bis-hydroxymethyl-4,6,6-trimethylcyclopenta[c]pyrrole-4-carboxamide ethanolate, m.p. 115°–120° C. The hydrate, m.p. 144°–147° C., was obtained in another run (12.0 g. from 15.0 g. of starting material) by precipitation from aqueous ethanol.

Following a procedure similar to that described in Example 7, the following compounds of Formula I were prepared where, in each instance, $R_1$ and $R_2$ are each hydrogen and $R_3$, $R_4$ and $R_5$ are each methyl.

Table 7

| Example | $R_6$ | $R_7$ | Wt. S.M. | Wt. Prod. | m.p.(°C.)/Solvent |
| --- | --- | --- | --- | --- | --- |
| 7A | $CH_2OH$ (1)<br>H (3) | $C_6H_5$ | 2.0 | 1.59 | 170–171/ethyl acetate |
| 7B | $CH_2OH$ (1)<br>$CH_3$ (3) | $C_6H_5$ | 2.3 | 1.8 | 184–185 |
| 7C | $CH_2OH$ (1)<br>COOH (3) | 4-$FC_6H_4$ | 3.0 | 2.0 | 140–190/ethyl acetate |
| 7D | $CH_2OH$ (1)<br>COOH (3) | $C_6H_5$ | 6.11 | 3.37 | 150–185/ethyl acetate |
| 7E | $CH_2OH$ (1)<br>H (3) | 4-$FC_6H_4$ | 2.0 | 1.3 | 182–183/benzene |
| 7F | H (1)<br>$CH_2OH$ (3) | $C_6H_5$ | 2.8 | 2.3 | 158–159/benzene |
| 7G | $CH_3$ (1) | $C_6H_5$ | 401 | 4.2[a] | 144–147/isopropanol |

Table 7-continued

| Example | R$_6$ | R$_7$ | Wt. S.M. | Wt. Prod. | m.p.(°C.)/Solvent |
|---|---|---|---|---|---|
| 7H | CH$_2$OCH(CH$_3$)$_2$ (3)<br>CH$_3$ (1) | C$_6$H$_5$ | 1.0 | 0.9 | 173–179/aqueous ethanol |
| 7J | CH$_2$OH (3)<br>CH$_2$OH | C$_6$H$_5$ | 6.2 | 1.0 | 116.5–118.5/ethanol |
| 7K | CH$_2$OH (1)<br>CH=CHCOOC$_2$H$_5$ (3) | C$_6$H$_5$ | 0.9 | 0.4 | 220–222.5/acetonitrile |
| 7L | CH$_2$OH (1)<br>C$_2$H$_5$ (3) | C$_6$H$_5$ | 2.4 | 1.7 | 119–120/ethanol-water |
| 7M | CH$_3$ (1)<br>CH$_2$OH (3) | C$_3$H$_7$ | 2.0 | 1.0 | 130–132/acetonitrile |
| 7N | CH$_2$OH (1)<br>H (3) | C$_3$H$_7$ | 3.0 | 2.6 | 144–146/ethanol-water |
| 7P | CH$_2$OH (1)<br>H (3) | 4-ClC$_6$H$_4$ | 2.0 | 1.3 | 212–213/acetonitrile |
| 7Q | CH$_2$OH (1)<br>H (3) | 3-ClC$_6$H$_4$ | 2.0 | 1.0 | 176–177/CH$_2$Cl$_2$-hexane |
| 7R | CH$_2$OH (1)<br>H (3) | 4-HOC$_6$H$_4$ | 1.3 | | 243–249 |

$^{(a)}$Obtained by recrystallizing 10 g. (of 444 g. obtained) of the corresponding 3-hydroxymethyl compound from isopropanol.

EXAMPLE 8

A solution of 10 g. (0.034 mole) of 2-phenyl-2,4,5,6-tetrahydro-1,3,4,6,6-pentamethylcyclopenta[c]pyrrole-4-carboxamide in 4.5 liters of chloroform was stirred under a high intensity light while bubbling air through the mixture for about sixteen hours. The mixture was then taken to dryness in vacuo and the residue dissolved in benzene and chromatographed on a column of activated magnesium silicate, the product being eluted first with benzene and then with ether. The combined eluates were diluted with ethyl acetate, and the solid which separated was collected and dried to give 1.05 g. of material which was shown by its n.m.r. and mass spectra and by chemical analysis to be 2-phenyl-3-formyl-2,4,5,6-tetrahydro-1,4,6,6-tetramethylcyclopenta[c]pyrrole-4-carboxamide, m.p. 201°–204° C. (Another sample showed m.p. 207°–209° C.)

In another experiment, a solution of 75 mg. of 2-phenyl-2,4,5,6-tetrahydro-1,3,4,6,6-pentamethylcyclopenta[c]pyrrole-4-carboxamide in a concentration of 1 mg./ml. in chloroform was exposed to sunlight for about five days and the solution then evaporated to a concentration of 10 mg./ml., chromatographed on alumina and eluted with 1:1 chloroform-methanol. A total of five bands was developed, the first of which yielded 7.8 mg. and the third 33.3 mg. of material both of whose mass spectra showed a molecular ion of 310 (calculated 308.4) and whose n.m.r. spectrum showed the first to be 2-phenyl-1-formyl-2,4,5,6-tetrahydro-3,4,6,6-tetramethylcyclopenta[c]pyrrole-4-carboxamide, identical with the compound described above in Example 1AW, and the third to be the isomeric 2-phenyl-3-formyl-2,4,5,6-tetrahydro-1,4,6,6-tetramethylcyclopenta[c]pyrrole-4-carboxamide.

EXAMPLE 9

2-Phenyl-1-formyl-2,4,5,6-tetrahydro-4,6,6-trimethylcyclopenta[c]pyrrole-4-carbonitrile (8.35 g., 0.03 mole) was combined with 4.6 ml. of 85% hydrazide hydrate, 5.25 g. of solid potassium hydroxide and 50 ml. of triethylene glycol, and the mixture was refluxed for one and one half hours under nitrogen. The low boiling components were distilled off until the pot temperature reached 205° C., and the mixture was then heated an additional two hours at that temperature. The mixture was cooled, poured into ice water, and extracted with ethyl acetate. The aqueous phase was acidified with concentrated sulfuric acid, and the solid which separated was collected and dried to give 6.2 g. of 2-phenyl-2,4,5,6-tetrahydro-1,4,6,6-tetramethylcyclopenta[c]pyrrole-4-carboxylic acid.

The latter (6.18 g., 0.22 mole) was dissolved in 70 ml. of tetrahydrofuran, the solution treated with 4.25 g. (0.026 mole) of N,N'-carbonyldiimidazole, and the solution stirred for six hours at room temperature. A solution of 5 ml. of liquid ammonia in 20 ml. of tetrahydrofuran was then added gradually and the solution stirred at room temperature for about fifteen hours. The solid which separated was collected and dissolved in ethyl acetate and the solution washed first with dilute alkali, then with brine, dried and taken to dryness. The pale yellow residual solid was recrystallized once from ethyl acetate and once from methanol to give 1 g. of 2-phenyl-2,4,5,6-tetrahydro-1,4,6,6-tetramethylcyclopenta[c]pyrrole-4-carboxamide, m.p. 185°–202° C.

EXAMPLE 10

A solution of 25 g. of 2-phenyl-2,4,5,6-tetrahydro-1,3,4,6,6-pentamethylcyclopenta[c]pyrrole-4-carboxamide (described in Example 1F) in 500 ml. of chloroform containing about 0.75% ethanol was stirred at ambient temperature for four days while bubbling air through the solution. The solution was then taken to dryness and the residue eluted with diethyl ether/hexane. There was thus obtained material having m.p. 95°–100° C. whose mass spectrum showed a molecular ion of 384 (calculated 384) and which was shown from its n.m.r. spectrum to be 2-phenyl-1,3-diethoxymethyl-2,4,5,6-tetrahydro-4,6,6-trimethylcyclopenta[c]pyrrole-4-carboxamide.

The latter, on reaction with hydrochloric acid in chloroform, afforded a mixture which was separated by chromatography into two components, the major component being 2-phenyl-3-formyl-2,4,5,6-tetrahydro-1,4,6,6-tetra-methylcyclopenta[c]pyrrole-4-carboxamide and the minor being the isomeric 2-phenyl-1-formyl-2,4,5,6-tetrahydro-3,4,6,6-tetramethylcyclopenta[c]pyrrole-4-carboxamide which were shown by their mass and n.m.r. spectra to be identical with the respective compounds described above in Example 8.

EXAMPLE 11

A solution of 2.0 g. (0.006 mole) of the 2-phenyl-2,4,5,6-tetrahydro-1,3-bis-hydroxymethyl-4,6,6-trimethylcyclopenta[c]pyrrole-4-carboxamide described in Example 7J in 50 ml. of methanol was treated with 0.11 g. of p-toluene-sulfonic acid, the solution was stirred at room temperature for an hour and a half and then taken to dryness. The residue was dissolved in methylene dichloride, the solution washed with saturated sodium bicarbonate and brine, then dried over sodium sulfate and taken to dryness, and the crude product recrystallized from benzene/hexane to give 2.2 g. of 2-phenyl-2,4,5,6-tetrahydro-1,3-bis-methoxymethyl-4,6,6-trimethylcyclopenta[c]pyrrole-4-carboxamide, m.p. 168°–169.5° C.

EXAMPLE 12

A mixture of 15.0 g. (0.05 mole) of 2-phenyl-2,4,5,6-tetrahydro-1,3,4,6,6-pentamethylcyclopenta[c]pyrrole-4-carboxamide (described in Example 1F), 15.0 g. (0.38 mole) of sodium hydroxide, 150 ml. of ethylene glycol and 1.0 ml. of water was refluxed in a stainless steel round bottom flask for two days. The mixture was then cooled, poured into about one liter of water and acidified with glacial acetic acid. The solid which separated was washed with water and recrystallized from methanol to give 8.0 g. of 2-phenyl-2,4,5,6-tetrahydro-1,3,4,6,6-pentamethylcyclopenta[c]pyrrole-4-carboxylic acid, m.p. 131°–136° C.

EXAMPLE 13

A stirred solution of 9.0 g. (0.03 mole) of 2-phenyl-2,4,5,6-tetrahydro-1,3,4,6,6-pentamethylcyclopenta[c]pyrrole-4-carboxylic acid (described in Example 12) in 100 ml. of anhydrous tetrahydrofuran was treated with 5.4 g. (0.033 mole) of N,N'-carbonyldiimidazole and the solution stirred at ambient temperature for eighteen hours. The resulting solution was then treated with 3.5 g. (0.04 mole) of 2-dimethylaminoethylamine in 50 ml. of tetrahydrofuran, and the mixture stirred for an additional six hours. The solution was then concentrated to dryness in vacuo. The residue was partitioned between 200 ml. of water and 100 ml. of ether, and the organic layer was separated, washed with brine, dried, and taken to dryness to give 10.8 g. of 2-phenyl-2,4,5,6-tetrahydro-1,3,4,6,6-pentamethylcyclopenta[c]pyrrole-4-{N-[2-(dimethylamino)ethyl]}carboxamide as a clear colorless oil.

It is contemplated that by following a procedure similar to that described above in Example 13, using the 2-phenyl-2,4,5,6-tetrahydro-1,3,4,6,6-pentamethylcyclopenta[c]pyrrole-4-carboxylic acid described in Example 12 and an appropriate tertiary amino-lower-alkylamine, the following compounds of Formula I can be prepared where, in each instance, $R_2$ is hydrogen; $R_3$, $R_4$, $R_5$ and $R_6$ are $CH_3$; $R_7$ is phenyl; and X is O.

Table 13

| Example | $R_1$ |
|---|---|
| 13A | $CH_2CH_2N(CH_2CH_2)_2O$ |
| 13B | $CH_2CH_2N(CH_2)_4$ |
| 13C | $CH_2CH_2N(CH_2)_5$ |

EXAMPLE 14

A suspension of 15.0 g. (0.05 mole) of 2-phenyl-2,4,5,6-tetrahydro-1,3,4,6,6-pentamethylcyclopenta[c]pyrrole-4-carboxylic acid (described in Example 12) and 6.0 g. (0.06 mole) of potassium bicarbonate in dimethylformamide was stirred at room temperature for two and one half hours at 60° C. for a half hour, then cooled and treated with 14 g. (0.1 mole) of methyl iodide in dimethylformamide and the mixture stirred overnight. The resulting dark solution was taken to dryness in vacuo, and the dark residual viscous oil was distilled in vacuo to give 5.9 g. of methyl 2-phenyl-2,4,5,6-tetrahydro-1,3,4,6,6-pentamethylcyclopenta[c]pyrrole-4-carboxylate, b.p. 130°–132° C./0.05 mm.

EXAMPLE 15

A solution of 9.0 g. (0.03 mole) of 2-phenyl-2,4,5,6-tetrahydro-1,3,4,6,6-pentamethylcyclopenta[c]-pyrrole-4-carboxylic acid (described in Example 12) in 50 ml. of anhydrous tetrahydrofuran, and the solution treated with 5.4 g. (0.033 mole) of N,N'-carbonyldiimidazole. The mixture was then treated with a solution of 2.9 g. (0.03 mole) of aniline in 25 ml. of tetrahydrofuran, the solution stirred at room temperature for twenty-four hours, and then taken to dryness in vacuo. The residue was partitioned between water and diethyl ether, and the ether layer was washed with brine, then dried and taken to dryness leaving 10.8 g. of a solid residue which was recrystallized twice from methanol to give 4.7 g. of 1-(2-phenyl-2,4,5,6-tetrahydro-1,3,4,6,6-pentamethycyclopenta[c]pyrrole-4-yl carbonyl)imidazole, m.p. 134°–136° C.

EXAMPLE 16

A mixture of 29.6 g. (0.1 mole) of 2-phenyl-2,4,5,6-tetrahydro-1,3,4,6,6-pentamethylcyclopenta[c]pyrrole-4-carboxamide (described in Example 1F) and 0.10 g. of cupric acetate monohydrate in 300 ml. of 4:6 methanol/benzene mixture was stirred under two atmosperes of oxygen for twenty hours. The resulting black solution was taken to dryness, and the residual dark semi-solid was dissolved in 300 ml. of methylene dichloride and the solution washed with water, then with saturated brine, charcoaled, filtered and taken to dryness. The residue was recrystallized twice from methanol to give 14.1 g. of a mixture of 2-phenyl-1-methoxymethyl-2,4,5,6-tetrahydro-3,4,6,6-tetramethylcyclopenta[c]-pyrrole-4-carboxamide and 2-phenyl-3-methoxymethyl-2,4,5,6-tetrahydro-1,4,6,6-tetramethylcyclopenta[c]pyrrole-4-carboxamide, m.p. 181°–193° C.

EXAMPLE 17

A mixture of 10 g. (0.032 mole) of 2-phenyl-1-formyl-2,4,5,6-tetrahydro-3,4,6,6-tetramethylcyclopenta[c]-pyrrole-4-carboxamide (described in Example 8) and 1.0 g. of 10% palladium-on-charcoal in 100 ml. of 2-(2-ethoxy)-ethoxyethanol was heated to reflux under nitrogen for eight hours and then cooled and allowed to stand at ambient temperature for about twelve hours. The catalyst was removed by filtration, the filtrate poured into water and the mixture extracted with benzene. The benzene extracts, after washing, drying and evaporation to dryness, gave a yellow gum which was triturated with ether and recrystallized from benzene to give 0.9 g. of 2-phenyl-2,4,5,6-tetrahydro-3,4,6,6-tetramethylcyclopenta[c]pyrrole-4-carboxamide, m.p. 186°–190° C.

EXAMPLE 18

A solution of 2.96 g. (0.01 mole) of 2-phenyl-1-formyl-2,4,5,6-tetrahydro-4,6,6-trimethylcyclopenta[c]- pyrrole-4-carboxamide (described in Example 1AV) in 30 ml. of benzene and 120 ml. of tetrahydrofuran was cooled to −5° C. under nitrogen and then treated with 5.7 ml. (0.012 mole) of a 2.1 molar solution of diethyl aluminum cyanide in benzene. The mixture was stirred at −5° to −10° C. for twenty minutes, then for one hour at ambient temperature, poured onto 150 g. of ice, acidified with 10 ml. of acetic acid and extracted with benzene. The benzene extracts yielded an amorphous foam which solidified on trituration with benzene. There was thus obtained 2.75 g. of 2-phenyl-1-(hydroxycyanomethyl)-2,4,5,6-tetrahydro-4,6,6-trimethylcyclopenta[c]pyrrole-4-carboxamide as the hemi-benzene solvate, slowly decomposes at 120° C., resolidifies and melts again at 142° C.

EXAMPLE 19

To a solution of 1.0 g. (0.003 mole) of 2-phenyl-1-hydroxymethyl-2,4,5,6-tetrahydro-4,6,6-trimethylcyclopenta[c]pyrrole-4-carboxamide (described in Example 7A) in 7 ml. of pyridine was added 570 mg. (0.004 mole) of 4-methylbenzoyl chloride. The reaction mixture was refrigerated for two days, poured into saturated sodium bicarbonate solution, extracted with methylene dichloride and the organic extracts dried and evaporated to dryness to give 1.3 g. of residue which was recrystallized from ethyl acetate to give 696 g. of 2-phenyl-1-(4-methylbenzoyloxymethyl)-2,4,5,6-tetrahydro-4,6,6-trimethylcyclopenta[c]pyrrole-4-carboxamide, m.p. 200°–204° C.

Using the procedure described in Example 19, the following compounds of Formula I, where in each case $R_1$, $R_2$ and $R_6$ (3-position) are each hydrogen, $R_3$, $R_4$ and $R_5$ are each $CH_3$ and $R_7$ is $C_6H_5$, were prepared from 2-phenyl-1-hydroxymethyl-2,4,5,6-tetrahydro-4,6,6-trimethylcyclopenta-[c]pyrrole-4-carboxamide and acetic anhydride or succinic anhydride.

EXAMPLE 20

To a solution of 1 g. (0.0025 mole) of 2-phenyl-1-(3-carboxypropionyloxymethyl)-2,4,5,6-tetrahydro-4,6,6-trimethylcyclopenta[c]pyrrole-4-carboxamide (described in Example 19B) in 10 ml. of tetrahydrofuran at 0°–5° C. was added anhydrous ammonia by passing the gas over the surface of the solution. The mixture was diluted with ether and the gummy solid which separated solidified on scratching to give 1.0 g. of the corresponding ammonium salt, m.p. 116°–118° C.

EXAMPLE 21

To a suspension of 2.96 g. (0.01 mole) of 2-phenyl-1-formyl-2,4,5,6-tetrahydro-4,6,6-trimethylcyclopenta[c]pyrrole-4-carboxamide (described in Example 1AV) in 50 ml. of tetrahydrofuran was added 12.9 ml. of a 0.16 molar solution of methyl lithium while cooling the mixture. After stirring for one hour at 0°–5° C. and for two hours at ambient temperature, the mixture was poured into ice/aqueous ammonium chloride and extracted with methylene dichloride. The extracts, on drying and evaporation to dryness, gave crude product which was recrystallized from methylene dichloride-heptane to give 1.91 g. of 2-phenyl-1-(1-hydroxyethyl)-2,4,5,6-tetrahydro-4,6,6-trimethylcyclopenta[c]-pyrrole-4-carboxamide, m.p. 135°–145° C. consisting of a mixture of the two possible racemic pairs. One of the pure racemates was obtained by recrystallization of 35 g. of the di-racemate mixture from aqueous ethanol to give 16 g. of a mono-racemate as the ethanolate, m.p. 165°–168° C.

Using a procedure similar to that described in Example 21 above, the following compounds of Formula I, where in each case $R_1$ and $R_2$ are each hydrogen and $R_3$, $R_4$ and $R_5$ are each $CH_3$ were prepared by reaction of an appropriate organo lithium with an appropriate 1- or 3-formyl-2,4,5,6-tetrahydro-4,6,6-trimethylcyclopenta[c]pyrrole-4-carboxamide.

Table 19

| Example | $R_6$ (1) | Wt. S.M. | Wt. Prod. | m.p.(°C.)/Solvent |
|---|---|---|---|---|
| 19A | $CH_2COOCH_2$ | 2.0 | 1.46 | 174–175/ethyl acetate |
| 19B | $HOOC(CH_2)_2COOCH_2$ | 2.0 | 0.9 | 152–154/ethyl acetate-hexane |

Table 21

| Example | $R_6$ | $R_7$ | Wt. S.M. | Wt. Prod. | m.p.(°C.)/Solvent |
|---|---|---|---|---|---|
| 21A | $CH_3$ (1) <br> $CHOHCH_3$ (3) | $C_6H_5$ | 3.0 | 1.09 | 108–111/ether-hexane |
| 21B | $CH_2\!\!=\!\!CHCHOH$ (1) <br> H (3) | $C_6H_5$ | 5.92 | 2.07 | 144–146/benzene |
| 21C | $CH_3$ (1) <br> $C_6H_5CHOH$ (3) | $C_6H_5$ | 6.0 | 4.12 | 151–154/acetonitrile |
| 21D | $CH_3$ (1) <br> $CH_2\!\!=\!\!CHCHOH$ (3) | $C_6H_5$ | 6.0 | 2.88 | 160–165/ethyl acetate |
| 21E | $C_4H_9CHOH$ (1) <br> H (3) | $C_6H_5$ | 5.92 | 2.4 | 75–80/- |
| 21F | $CH_3$ (1) <br> $C(CH_3)_2OH$ (3) | $C_6H_5$ | 2.0 | 0.68 | 184–186/ether-hexane |
| 21G | $C_2H_5CHOH$ (1) <br> H (3) | $C_6H_5$ | 2.96 | 2.62 | 155–156/ether-heptane |
| 21H | $CH\!\!\equiv\!\!CCHOH$ (1) <br> H (3) | $C_6H_5$ | 2.96 | 1.6 | 178–179/ether-hexane |
| 21J | $C_3H_7CHOH$ (1) <br> H (3) | $C_6H_5$ | 5.82 | 5.5 | 139–140/ether-hexane |
| 21K | $(CH_3)_3COCOCH_2CHOH$ (1) <br> H (3) | $C_6H_5$ | 2.96 | 2.7 | 142–143/$CH_2Cl_2$-heptane |
| 21L | $CH_2\!\!=\!\!CHCH_2CHOH$ (1) <br> H (3) | $C_6H_5$ | 5.82 | 4.59 | 108–109/$CH_2Cl_2$-hexane |
| 21M | $C_2H_5OCOC\!\!\equiv\!\!CCHOH$ (1) <br> H (3) | $C_6H_5$ | 5.82 | 4.59 | 85–87/ether-hexane |
| 21N | $CH_3CHOH$ (1) | $C_3H_7$ | 3.78 | 0.46 | 149–150/$CH_2Cl_2$- |

Table 21-continued

| Example | $R_6$ | $R_7$ | Wt. S.M. | Wt. Prod. | m.p.(°C.)/Solvent |
|---|---|---|---|---|---|
| 21P | H (3)<br>$C_6H_5CHOH$ (1) | $C_3H_7$ | 4.0 | 1.85 | heptane<br>144–146/$CH_2Cl_2$ |
| 21Q | H (3)<br>4-$CH_3OC_6H_4CHOH$ (1)[a] | $C_6H_5$ | 5.02 | 1.73 | 183–185/acetonitrile |
| 21R | H (3)<br>$CH_3CHOH$ (1) | 3-$ClC_6H_4$ | 3.30 | 1.07 | 142–144/ether-hexane |
| 21S | H (3)<br>$CH_3CHOH$ (1) | 4-$ClC_6H_4$ | 2.55 | 1.2 | 198–200/$CH_2Cl_2$-hexane |

[a]4-Methoxyphenyl magnesium bromide used as the organo metallic reagent.

EXAMPLE 22

A solution of 5.82 g. (0.02 mole) of 2-phenyl-1-formyl-2,4,5,6-tetrahydro-4,6,6-trimethylcyclopenta[c]pyrrole-4-carboxamide in 150 ml. of tetrahydrofuran was cooled to 0°–5° C. and treated with stirring over a period of two hours with 24.4 ml. (0.02 mole) of a 1.8 molar solution of propyl magnesium chloride in diethyl ether. When addition was complete, the mixture was allowed to stand for sixteen hours at ambient temperature and then poured onto a mixture of ice and saturated ammonium chloride solution and the mixture extracted with diethyl ether. The organic extracts were combined, dried over magnesium sulfate, and the solvent removed to give a residual solid, which was recrystallized from hexane/benzene to give 2.46 g. of 2-phenyl-1-[1-(2-butenyl)]-2,4,5,6-tetrahydro-4,6,6-trimethylcyclopenta[c]pyrrole-4-carboxamide, m.p. 156°–157° C.

EXAMPLE 22A

A solution of 3.0 g. of 2-phenyl-1-(1-hydroxyethyl)-2,4,5,6-tetrahydro-4,6,6-trimethylcyclopenta[c]pyrrole-4-carboxamide in 150 ml. of benzene was boiled for one hour, then taken to dryness in vacuo and the residue recrystallized from ethanol to give 2.2 g. of 2-phenyl-1-ethenyl-2,4,5,6-tetrahydro-4,6,6-trimethylcyclopenta[c]pyrrole-4-carboxamide, m.p. 195°–196° C.

EXAMPLE 23

To 40 ml. of 90% sulfuric acid cooled to 0°–5° C. was added 4.0 g. (0.012 mole) of 2-phenyl-1-(hydroxycyanomethyl)-2,4,5,6-tetrahydro-4,6,6-trimethylcyclopenta[c]pyrrole-4-carboxamide (described above in Example 18), and the mixture was stirred at 0°–5° C. for thirteen hours. The mixture was then poured onto ice, extracted with ether, and the ether extracts combined and set aside. Extraction of the aqueous layer with methylene dichloride and isolation of the organic material from the extracts afforded material which was recrystallized from benzene to give 1.0 g. of 2-phenyl 1-(aminocarbonylhydroxymethyl)-2,4,5,6-tetrahydro-4,6,6-trimethylcyclopenta[c]pyrrole-4-carboxamide as the hemi-benzene solvate, m.p. 129°–131° C.

EXAMPLE 24

A solution of 1.2 g. (0.003 mole) of 2-phenyl-3-carbethoxyethyl-2,4,5,6-tetrahydro-1,4,6,6-tetramethylcyclopenta[c]pyrrole-4-carboxamide (described above in Example 1BC) in 7.86 ml. of a 1 molar solution of potassium hydroxide in methanol containing 5 percent water was stirred at ambient temperature for ten hours and then extracted with ether. The aqueous layer was then acidified with excess 6 N hydrochloric acid and extracted with ether. The combined ether extracts, on drying and evaporation to dryness, afforded a solid residue which was recrystallized from acetonitrile to give 1.0 g. of 2-phenyl-3-carboxyethyl-2,4,5,6-tetrahydro-1,4,6,6-tetramethylcyclopenta[c]pyrrole-4-carboxamide, m.p. 187°–188° C.

EXAMPLE 24A

Proceeding in a manner similar to that described in Example 24 above, a solution of 7.72 g. (0.02 mole) of 2-(4-carbethoxyphenyl)-2,4,5,6-tetrahydro-1,3,4,6,6-pentamethylcyclopenta[c]pyrrole-4-carboxamide (described above in Example 1BK) was dissolved in a solution of 40 ml. of ethanol and 40 ml. of water, treated with 0.86 g. of sodium hydroxide and the solution stirred and refluxed on a steam bath for an hour and a half. The mixture was worked up in the manner described in Example 24 to give 5.05 g. of 2-(4-carboxyphenyl)-2,4,5,6-tetrahydro-1,3,4,6,6-pentamethylcyclopenta[c]pyrrole-4-carboxamide, m.p. 285°–287° C.

EXAMPLE 25

It is contemplated that reaction of an appropriate 2,4,5,6-tetrahydro-1,3,4,6,6-pentamethylcyclopenta[c]pyrrole-4-carbonitrile in an autoclave at 150°–160° C. with an ethanol solution saturated with anhydrous ammonia and anhydrous hydrogen sulfide would afford the following compounds of Formula I where, in each instance, $R_1$ and $R_2$ are hydrogen; $R_3$, $R_4$, $R_5$ and both $R_6$ groups are each $CH_3$; and X is S.

Table 25

| Example | $R_7$ |
|---|---|
| 25A | $CH_3$ |
| 25B | $CH_2CH_2CH_2N(CH_3)_2$ |
| 25C | $CH_2CH_2C_6H_5$ |
| 25D | $C_6H_5$ |
| 25E | 2-pyridyl |
| 25F | $CH_2CH_2CSNH_2$ |

It is contemplated that following the procedures described below, the compounds described in Examples 26–32 can be prepared.

EXAMPLE 26

Reaction of the ethyl 4-carbamoyl-2,4,5,6-tetrahydro-1,3,4,6,6-pentamethylcyclopenta[c]pyrrole-2-acetate described above in Example 1AC with alcoholic sodium hydroxide and isolation of the product from an acid or neutral medium affords 4-carbamoyl-2,4,5,6-tetrahydro-1,3,4,6,6-pentamethylcyclopenta[c]pyrrole-2-acetic acid.

EXAMPLE 27

Reaction of the 2-(4-carboxyphenyl)-2,4,5,6-tetrahydro-1,3,4,6,6-pentamethylcyclopenta[c]pyrrole-4-carboxamide described above in Example 24A with methanol in the presence of a small amount of a mineral acid affords 2-(4-carbomethoxyphenyl)-2,4,5,6-tetrahydro- 1,3,4,6,6-pentamethylcyclopenta[c]pyrrole-4-carboxamide.

EXAMPLE 28

Reaction of the 2-(3-methylmercaptophenyl)-2,4,5,6-tetrahydro-1,3,4,6,6-pentamethylcyclopenta[c]pyrrole-4-carboxamide described above in Example 1CK with one molar equivalent of performic acid in acetone at room temperature affords 2-(3-methylsulfinylphenyl)-2,4,5,6-tetrahydro-1,3,4,6,6-pentamethylcyclopenta[c]pyrrole-4-carboxamide.

EXAMPLE 29

Reaction of the 2-(3-methylmercaptophenyl)-2,4,5,6-tetrahydro-1,3,4,6,6-pentamethylcyclopenta[c]pyrrole-4-carboxamide described above in Example 1CK with two molar equivalents of performic acid in acetone at room temperature affords 2-(3-methylsulfonylphenyl)-2,4,5,6-tetrahydro-1,3,4,6,6-pentamethylcyclopenta[c]pyrrole-4-carboxamide.

EXAMPLE 30

Reaction of the 2-phenyl-2,4,5,6-tetrahydro-1,3-diformyl-4,6,6-trimethylcyclopenta[c]pyrrole-4-carboxamide described above in Example 1AB with two molar equivalents of perbenzoic acid in acetone at room temperature affords 2-phenyl-2,4,5,6-tetrahydro-4,6,6-trimethylcyclopenta[c]-pyrrole-4-carboxamido-1,3-dicarboxylic acid.

EXAMPLE 31

Reaction of the 2-phenyl-2,4,5,6-tetrahydro-4,6,6-trimethylcyclopenta[c]pyrrole-4-carboxamido-1,3-dicarboxylic acid described above in Example 30 with methanol in the presence of a small amount of a mineral acid affords dimethyl 2-phenyl-2,4,5,6-tetrahydro-4,6,6-trimethylcyclopenta[c]pyrrole-4-carboxamido-1,3-dicarboxylate.

EXAMPLE 32

Reaction of 1-phenyl-2,4,5,6-tetrahydro-1,3,4,6,6-pentamethylcyclopenta[c]pyrrole-4-carbonitrile with one molar equivalent of diisobutyl aluminum hydride in tetrahydrofuran, and, without isolation of the product, oxidation of the resulting material with oxygen affords 2-phenyl-2,4,5,6-tetrahydro-1,3,4,6,6-pentamethylcyclopenta[c]pyrrole-4-carboxamide.

BIOLOGICAL TEST RESULTS

Data obtained on administration in rats of the compounds of Formula I in the anti-secretory and the reserpine-induced anti-ulcer tests are given in terms of the % increase in the pH of gastric fluid over control animals and the % reduction in ulcer score over control animals. Doses are expressed in mg./kg., and unless noted otherwise by the designation i.p., s.c. and i.d. representing intraperitoneal, subcutaneous and intraduodenal, respectively, were obtained on oral administration. Compounds are considered active if any measurable increase in the pH or decrease in ulcer score over controls are obtained, although for purposes of further evaluation for possible ultimate commercial development, compounds were not considered further unless an increase in pH in the anti-secretory test of 80% or a reduction of 30% in the ulcer score in the anti-ulcer test were obtained. The compounds are identified by the Example number above where they are disclosed.

| Example | Dose | % pH Increase | % Reduction Ulcer Score |
|---|---|---|---|
| 1 | 25 | 9 | 60 |
|   | 50 | 50 | 60 |
|   | 100 | 84 | 100 |
|   | 200 | 96 | 100 |
| 1A |  | Inactive | Inactive |
| 1B | 100 | 20 | 40 |
| 1C | 100 | 24 | Inactive |
| 1D | 100 | 7 | Inactive |
| 1E | 100 | 4 | Inactive |
| 1F | 12.5 | 41 | — |
|   | 25 | 52 | 73 |
|   | 50 | 75 | 100 |
|   | 100 | 100 | 100 |
| 1G | 25 | — | 40 |
|   | 50 | 55 | 60 |
|   | 100 | 93 | — |
|   | 100 | 95 | 100 |
| 1H | 25 | 56 | 60 |
|   | 50 | 80 | 100 |
|   | 100 | 93 | 100 |
| 1J | 100 | 4 | 60 |
| 1K | 25 | — | 100 |
|   | 50 | — | 100 |
|   | 100 | 46 | 100 |
|   | 200 | 49 | — |
| 1L | 100 | 10 | Inactive |
| 1M | 100 | 16 | Inactive |
| 1N | 100 | 35 | 70 |
| 1P | 100 | 45 | 100 |
| 1Q | 100 | 20 | 80 |
| 1R | 100 | 16 | Inactive |
| 1S | 100 | 27 | Inactive |
| 1T | 50 | — | 80 |
|   | 100 | 47 | 90 |
| 1U | 100 | 9 | Inactive |
| 1V | 25 | — | 80 |
|   | 50 | 32 | 100 |
|   | 100 | 45 | — |
|   | 100 | 64 | 100 |
| 1W | 100 | 20 | 20 |
| 1X | 100 | 5 | Inactive |
| 1Y | 100 | 145 | 100 |
| 1Z | 100 | 77 | 40 |
| 1AA | 100 | 26 | 40 |
| 1AB | 100 | 18 | Inactive |
| 1AC | 100 | 4 | Inactive |
| 1AD | 25 | 3 | — |
|   | 50 | 11 | — |
|   | 100 | 16 | Inactive |
| 1AE | 50 | 157 | 100 |
|   | 100 | 253 | — |
|   | 200 | 400 | — |
| 1AF | 25 | — | 20 |
|   | 50 | 20 | — |
|   | 100 | 21 | — |
| 1AG | 100 | Inactive | 20 |
| 1AH | 100 | Inactive | 40 |
| 1AK | 25 | 48 | 20 |
|   | 50 | 110 | — |
|   | 100 | 120 | — |
| 1AL | 25 | 33 | — |
|   | 50 | 75 | 100 |
|   | 100 | 325 | — |
| 1AM | 100 | 14 | 100 |
| 1AN | 100 | 54 | 80 |
| 1AP | 50 | 8 | 80 |
| 1AQ | 100 | 10 | 20 |
| 1AR | 100 | 18 | Inactive |
| 1AS | 100 | 27 | 100 |
| 1AT | 12.5 | 236 | — |
| 1AU | 50 | — | 40 |
|   | 100 | 68 | — |
| 1AV | 50 | — | 100 |
|   | 100 | 38 | — |
| 1AW | 100 | 38 | 40 |
| 1AX | 100 | Inactive | 20 |
| 1AY | 100 | Inactive | 20 |
| 1BA | 100 | Inactive | — |
|   | 100 i.p. | 50 | — |
| 1BB | 100 | 10 | — |
|   | 100 i.p. | 60 | — |

-continued

| Example | Dose | % pH Increase | % Reduction Ulcer Score |
|---|---|---|---|
| 1BC | 100 | 20 | — |
|  | 100 i.p. | 20 | — |
| 1BD | 100 | 10 | — |
|  | 100 i.p. | 20 | — |
| 1BE | 100 | 10 | — |
|  | 100 i.p. | 10 | — |
| 1BF | 100 | Inactive | — |
|  | 100 i.p. | 20 | — |
| 1BG | 100 | 10 | — |
|  | 100 i.p. | 40 | — |
| 1BH | 100 | Inactive | — |
|  | 200 | 10 | — |
|  | 100 i.p. | 20 | — |
| 1BJ | 200 | 30 | — |
|  | 100 i.p. | 40 | — |
| 1BK | 100 | Inactive | — |
|  | 100 i.p. | 118 | — |
| 1BL | 100 | 9 | — |
|  | 200 | 18 | — |
|  | 50 s.c. | 9 | — |
|  | 50 i.d. | 18 | — |
| 1BM | 100 | Inactive | — |
|  | 100 i.p. | 155 | — |
| 1BN | 200 | 10 | — |
|  | 100 s.c. | 20 | — |
| 1BP | 200 | Inactive | — |
|  | 100 i.p. | 10 | — |
| 3 | 100 | 72 | 100 |
| 5 | 100 | 15 | Inactive |
| 7 | 100 | 8 | 60 |
| 7A | 12.5 | 45 | — |
|  | 25 | 228 | — |
|  | 50 | 445 | — |
|  | 100 | 480 | — |
| 7B | 12.5 | Inactive | 60 |
|  | 25 | 8 | 80 |
|  | 50 | 163 | — |
|  | 100 | 399 | — |
| 7C | 100 | 14 | 20 |
| 7D | 100 | Inactive | 60 |
| 7E | 100 | 42 | Inactive |
| 7F | 25 | Inactive | — |
|  | 50 | 79 | 80 |
|  | 100 | 244 | — |
| 7G | 100 | 18 | — |
| 7H | 12.5 | Inactive | — |
|  | 25 | 45 | — |
|  | 50 | 118 | — |
|  | 100 | 355 | — |
| 7K | 100 | 20 | — |
|  | 100 i.p. | 60 | — |
| 7L | 50 | 9 | — |
|  | 100 | 45 | — |
|  | 200 | 260 | — |
|  | 25 s.c. | 27 | — |
|  | 50 s.c. | 36 | — |
| 7M | 100 | 145 | — |
|  | 200 | 300 | — |
|  | 100 s.c. | 509 | — |
| 7N | 100 | 18 | — |
|  | 100 i.p. | 127 | — |
| 7P | 25 | Inactive | — |
|  | 200 | Inactive | — |
|  | 25 s.c. | Inactive | — |
|  | 25 i.d. | 10 | — |
|  | 100 i.p. | 45 | — |
| 7Q | 200 | 10 | — |
|  | 100 i.p. | 30 | — |
| 7R | 50 | 160 | — |
|  | 100 | 182 | — |
|  | 200 | 400 | — |
|  | 100 i.p. | 470 | — |
|  | 50 s.c. | 210 | — |
|  | 50 i.d. | 110 | — |
| 8 | 50 | Inactive | — |
|  | 100 | — | Inactive |
| 9 | 50 | 10 | 100 |
|  | 100 | 140 | — |
| 11 | 100 | 17 | Inactive |
| 13 | 50 | — | Inactive |
|  | 100 | 16 | 80 |
| 15 | 100 | Inactive | 80 |
| 16 | 100 | 51 | 75 |
| 17 | 50 | Inactive | — |
|  | 100 | 11 | — |
| 18 | 100 | 188 | — |
| 19 | 100 | 27 | 40 |
| 19A | 100 | 73 | 100 |
| 19B | 100 | 336 | — |
| 20 | 25 | — | 80 |
|  | 50 | 128 | — |
|  | 100 | 166 | — |
|  | 200 | 530 | — |
| 21 | 12.5 | 31 | — |
|  | 25 | 289 | — |
|  | 50 | 565 | — |
|  | 100 | 580 | — |
| 21A | 100 | 16 | — |
| 21B | 25 | 7 | — |
|  | 50 | 587 | — |
|  | 100 | 600 | — |
| 21C | 100 | 8 | — |
| 21D | 100 | 4 | — |
| 21E | 100 | 24 | — |
| 21F | 100 | 14 | — |
| 21G | 25 | 32 | — |
|  | 50 | 116 | — |
|  | 100 | 458 | — |
| 21H | 100 | 9 | — |
|  | 200 | 300 | — |
| 21J | 100 | 64 | — |
|  | 200 | 182 | — |
| 21K | 200 | Inactive | — |
|  | 100 i.p. | 160 | — |
| 21L | 100 | 73 | — |
|  | 200 | 210 | — |
| 21M | 100 | 9 | — |
|  | 100 i.p. | 9 | — |
|  | 50 i.d. | 64 | — |
| 21N | 100 | 36 | — |
| 21P | 100 | Inactive | — |
|  | 100 i.p. | 70 | — |
| 21Q | 100 | Inactive | — |
|  | 100 i.p. | 10 | — |
| 21R | 200 | 10 | — |
|  | 100 i.p. | 20 | — |
| 21S | 200 | Inactive | — |
|  | 100 i.p. | 9 | — |
| 22 | 100 | Inactive | — |
|  | 100 i.p. | 27 | — |
| 22A | 100 | 10 | — |
|  | 100 i.p. | 60 | — |
| 23 | 100 | 10 | — |
|  | 100 i.p. | 20 | — |
| 24 | 100 | 10 | — |
|  | 100 i.p. | 110 | — |
| 24A | 100 | 10 | — |
|  | 100 i.p. | 20 | — |

Although the species of Examples 1A and 8 were found inactive in both the anti-secretory and anti-ulcer tests, they are nevertheless useful as intermediates for preparing compounds which are useful as anti-secretory and/or anti-ulcer agents, the species of Example 1A being used to prepare the species of Example 4 (identical with the species of Example 1AL), and the species of Example 8 being used to prepare the species of Example 7H.

We claim:

1. A compound having the formula

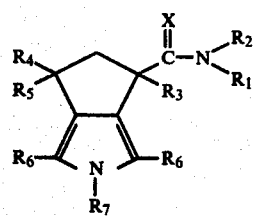

where X is O or S; $R_1$ and $R_2$ are each hydrogen or loweralkyl; each of $R_3$, $R_4$ and $R_5$ is hydrogen or methyl; each $R_6$ group is the same or different hydrogen, phenyl-lower-alkyl, methyl or lower-alkenyl; and $R_7$ is 2-, 3- or 4-pyridyl, and wherein the phenyl-lower-alkyl group can be further substituted in the phenyl nucleus by a single methylenedioxy or loweralkoxy group or by from one to three, the same or different, members of the group consisting of lower-alkyl, halogen, hydroxy, trifluoromethyl, lower-alkanoylamino, amino, di-lower-alkylamino, di-lower-alkylaminomethyl, carboxy, carboxamido, carbo-lower-alkoxy, lower-alkylmercapto, lower-alkylsulfinyl, lower-alkylsulfonyl, nitro and sulfamoyl except that both $R_6$ groups are not simultaneously hydrogen.

2. A compound having the formula

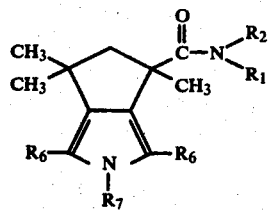

where $R_1$ and $R_2$ are each hydrogen or lower alkyl; each $R_6$ group is the same or different hydrogen, methyl or lower-alkenyl; and $R_7$ is 2- or 4-pyridyl except that both $R_6$ groups are not simultaneously hydrogen.

3. A compound according to claim 2 where each of $R_1$ and $R_2$ is hydrogen; and both $R_6$ groups are simultaneously methyl.

4. 2-(2-Pyridyl)-2,4,5,6-tetrahydro-1,3,4,6,6-pentamethylcyclopenta[c]pyrrole-4-carboxamide according to claim 3.

5. 2-(4-Pyridyl)-2,4,5,6-tetrahydro-1,3,4,6,6-pentamethylcyclopenta[c]pyrrole-4-carboxamide according to claim 3.

* * * * *